(12) United States Patent
Cheng et al.

(10) Patent No.: US 9,989,492 B1
(45) Date of Patent: Jun. 5, 2018

(54) MOBILE ELECTROCHEMICAL AIR QUALITY METER

(71) Applicant: Maxim Integrated Products, Inc., San Jose, CA (US)

(72) Inventors: Jim Chih-Min Cheng, Fremont, CA (US); Eric P. Lee, Mountain View, CA (US); Xiaoming Yan, Campbell, CA (US); Paul G. Schroeder, San Jose, CA (US); Albert Song, San Jose, CA (US)

(73) Assignee: Maxim Integrated Products, Inc., San Jose, CA (US)

( * ) Notice: Subject to any disclaimer, the term of this patent is extended or adjusted under 35 U.S.C. 154(b) by 128 days.

(21) Appl. No.: 15/070,681

(22) Filed: Mar. 15, 2016

Related U.S. Application Data

(63) Continuation-in-part of application No. 14/863,251, filed on Sep. 23, 2015.

(60) Provisional application No. 62/134,738, filed on Mar. 18, 2015.

(51) Int. Cl.
  *G01N 27/416* (2006.01)
  *G01N 27/40* (2006.01)
  *G01N 27/404* (2006.01)

(52) U.S. Cl.
  CPC ......... *G01N 27/4166* (2013.01); *G01N 27/40* (2013.01); *G01N 27/4045* (2013.01)

(58) Field of Classification Search
  CPC .................. G01N 27/404; G01N 27/4045
  See application file for complete search history.

(56) References Cited

U.S. PATENT DOCUMENTS

| | | | | |
|---|---|---|---|---|
| 5,522,908 A | * | 6/1996 | Frey | A47L 9/14 55/309 |
| 6,098,523 A | * | 8/2000 | Warburton | G01D 18/00 204/290.01 |
| 6,305,214 B1 | * | 10/2001 | Schattke | G01N 27/4045 204/412 |
| 2011/0100813 A1 | * | 5/2011 | Davis | G01N 27/40 204/415 |

* cited by examiner

*Primary Examiner* — Alexander S Noguerola
(74) *Attorney, Agent, or Firm* — Kevin E. West; Advent, LLP

(57) ABSTRACT

According to various embodiments of this disclosure, an electrochemical sensor/cell includes a substrate with a cavity formed on a first side of the substrate, an ionic conductor is disposed within the cavity, and a lid assembly positioned over the cavity. The lid assembly may include a plurality of electrodes attached to a glass or ceramic panel. The glass or ceramic panel may have one or more apertures allowing gas to flow therethrough. The plurality of electrodes include a working electrode configured to react a molecular species (e.g., gas or aerosolized substance) that diffuses through the one or more apertures, wherein said reaction produces ions mobile in the ionic conductor between two or more of the plurality of electrodes. The lid assembly may further include a three-phase interface positioned over at least a portion of the plurality of electrodes.

19 Claims, 10 Drawing Sheets

MOBILE ELECTROCHEMICAL AIR QUALITY METER

CROSS-REFERENCE TO RELATED APPLICATIONS

The present application is a continuation-in-part (CIP) of U.S. Non-Provisional application Ser. No. 14/863,251, filed Sep. 23, 2015, and titled "MOBILE ELECTROCHEMICAL AIR QUALITY METER," which claims the benefit under 35 U.S.C. § 119(e) of U.S. Provisional Application Ser. No. 62/134,738, filed Mar. 18, 2015, and titled "MOBILE ELECTROCHEMICAL AIR QUALITY METER." U.S. Non-Provisional application Ser. No. 14/863,251 and U.S. Provisional Application Ser. No. 62/134,738 are incorporated herein by reference in their entireties.

BACKGROUND

An electrochemical cell is a device capable of either deriving electrical energy from chemical reactions or facilitating chemical reactions through the introduction of electrical energy. Electrochemical cells are integral components of electrochemical sensors, which utilize electrodes to produce a current that is related to a detected amount of a molecular species allowing for the measurement of the concentration of the molecular species (e.g., gas or aerosolized substance) in a mixture of fluids (e.g., in air). Electrochemical sensors/cells can be incorporated in devices that measure environmental pollutants, such carbon monoxide detectors, and may also be used to measure breath alcohol. Because they require very little power to operate, electrochemical sensors/cells have been widely used in personal safety devices that measure toxic gases.

Plastic welding by laser or adhesive has been done previously with metal wire vias or planar printed electrical contacts to seal electrochemical cells. Also, layer-by-layer assembly of plastics with preformed adhesives has been done, where high temperature processes like platinum activation or printed electronic ink curing are done first, followed by electrolyte addition and sealing. Generally in electrochemical gas cells the working electrodes, and in planar schemes, all electrodes, are close to the gas inlet (e.g., located on a lid with a gas permeable membrane aperture). Several designs and processes address plastic-to-plastic assembly and provide in-plane electrical connections, but are typically unsuitable for integration of heterogeneous cell materials (e.g., glass-to-plastic, etc.) and provide electrical contacts near the top (gas inlet) side in the planar case, or through the sidewall in the case of metal wires. There is a need in the art for similar or dissimilar electrochemical cell materials, especially incorporating planar electrodes, to be attached robustly and sealed with a minimal bond width and sidewall thickness and in a manner that allows for electrical connections (vias) to the bottom side (opposite the gas inlet), so as to have an upward facing gas inlet and bottom side electrical connections suitable for connecting via a plug connector or low temperature die attach to an electrical circuit or printed circuit board. In such an arrangement the gas inlet is facing away from the PCB, a desirable orientation for common applications requiring an input aperture in a cover case or for incorporation of special gas filters that would be challenging or impractical if the filter had to be on the same side as the electrical connections. Electrochemical cell materials with high rigidity that can be processed into highly anisotropic features including reservoir cavities and vias are also desirable for minimizing the overall size of the cell.

SUMMARY

The present disclosure is directed to an air quality meter including one or more electrochemical sensor/cells for detecting one or more molecular species. According to various embodiments disclosed herein, an electrochemical sensor/cell includes a substrate with a cavity formed on a first side of the substrate, an ionic conductor (e.g., an electrolyte solution) is disposed within the cavity, and a lid assembly positioned over the cavity. In some embodiments, the lid assembly may include a plurality of electrodes attached to a glass or ceramic panel. The glass or ceramic panel may have one or more apertures allowing gas to flow therethrough. The plurality of electrodes include a working electrode configured to react (e.g., oxidize or reduce) a molecular species (e.g., gas or aerosolized substance) that diffuses through the one or more apertures, wherein said reaction produces ions mobile in the ionic conductor between two or more of the plurality of electrodes. The lid assembly may further include a three-phase interface positioned over at least a portion of the plurality of electrodes. The three-phase interface can include at least a hydrophobic layer and a catalyst layer. In some embodiments, for example, the three-phase interface can comprise Pt-Carbon paper mounted over at least a portion of the electrodes and possibly over at least a portion of the one or more apertures.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

Figure 6A:
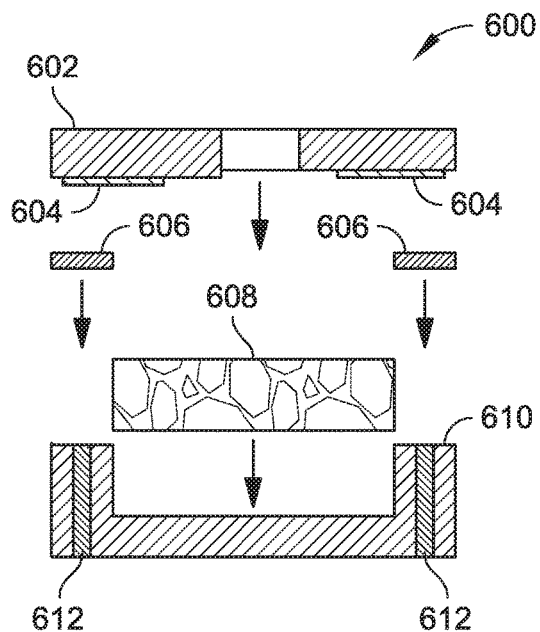

FIG. 6A schematically illustrates a method of sealing a lid onto a base of an electrochemical sensor/cell and simultaneously forming electrical contacts between the lid and vias in the base, in accordance with an embodiment of this disclosure.

Figure 6B:
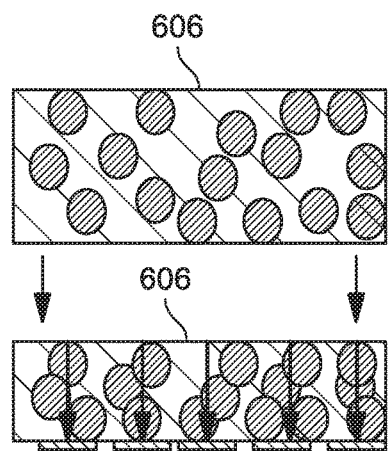

FIG. 6B schematically illustrates vertical conductive paths being formed in anisotropic conductive paste (ACP) or film (ACF) that is used to seal the lid to the base (as shown in FIG. 6A), where the conductive paths are formed when the ACP or ACF is compressed and cured.

Figure 6C:
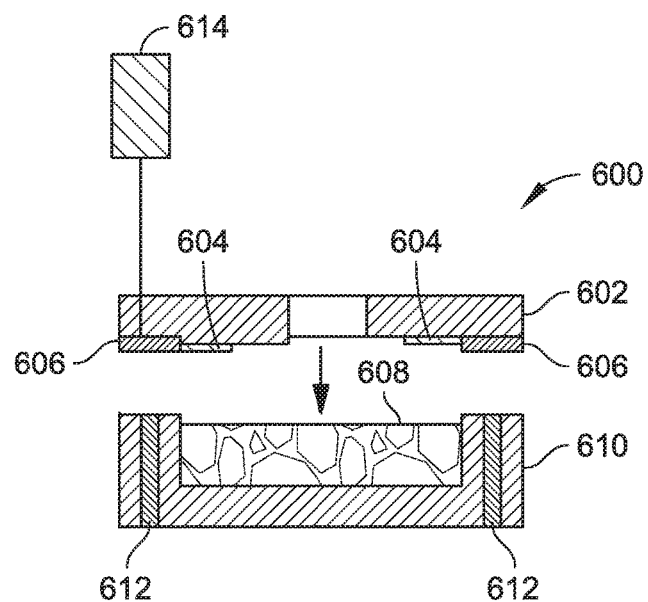

FIG. 6C schematically illustrates a method of sealing a lid onto a base of an electrochemical sensor/cell and simultaneously forming electrical contacts between the lid and vias in the base, in accordance with an embodiment of this disclosure.

Figure 7:
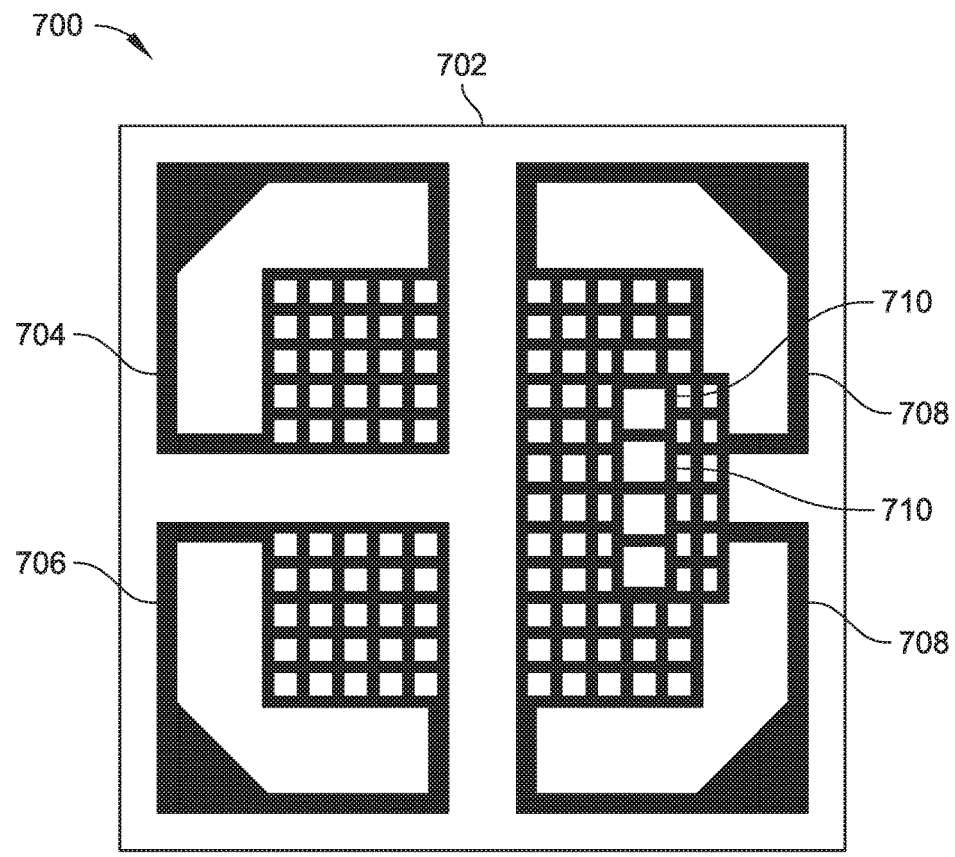

FIG. 7 shows a bottom view of a lid assembly in accordance with an embodiment of this disclosure.

Figures 8A, 8B:
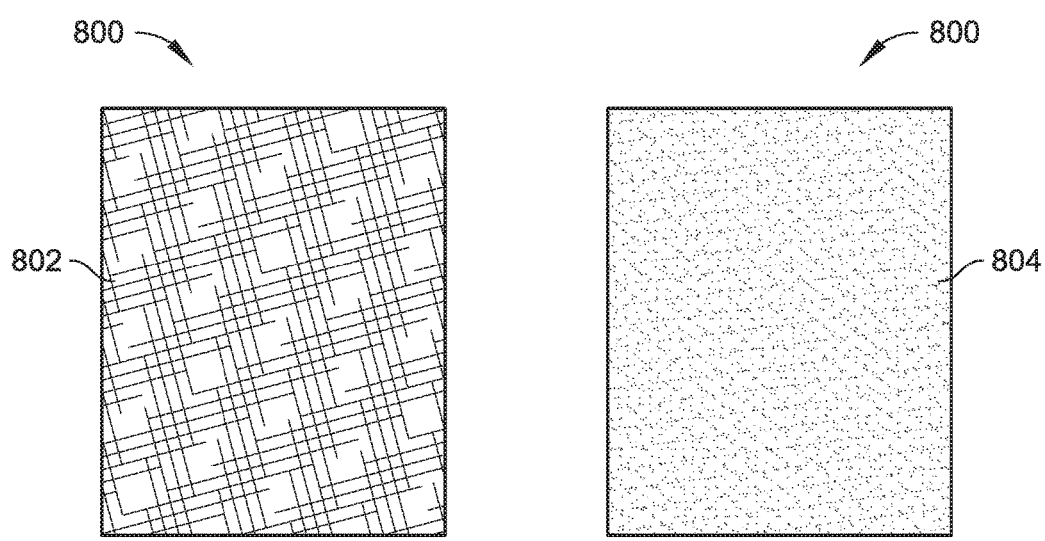

FIG. 8A shows a platinum (Pt) loaded side of a Pt loaded Carbon paper (sometimes referred to as "Pt-Carbon paper").

FIG. 8B shows a non-Pt loaded side of the Pt-Carbon paper.

Figure 9:
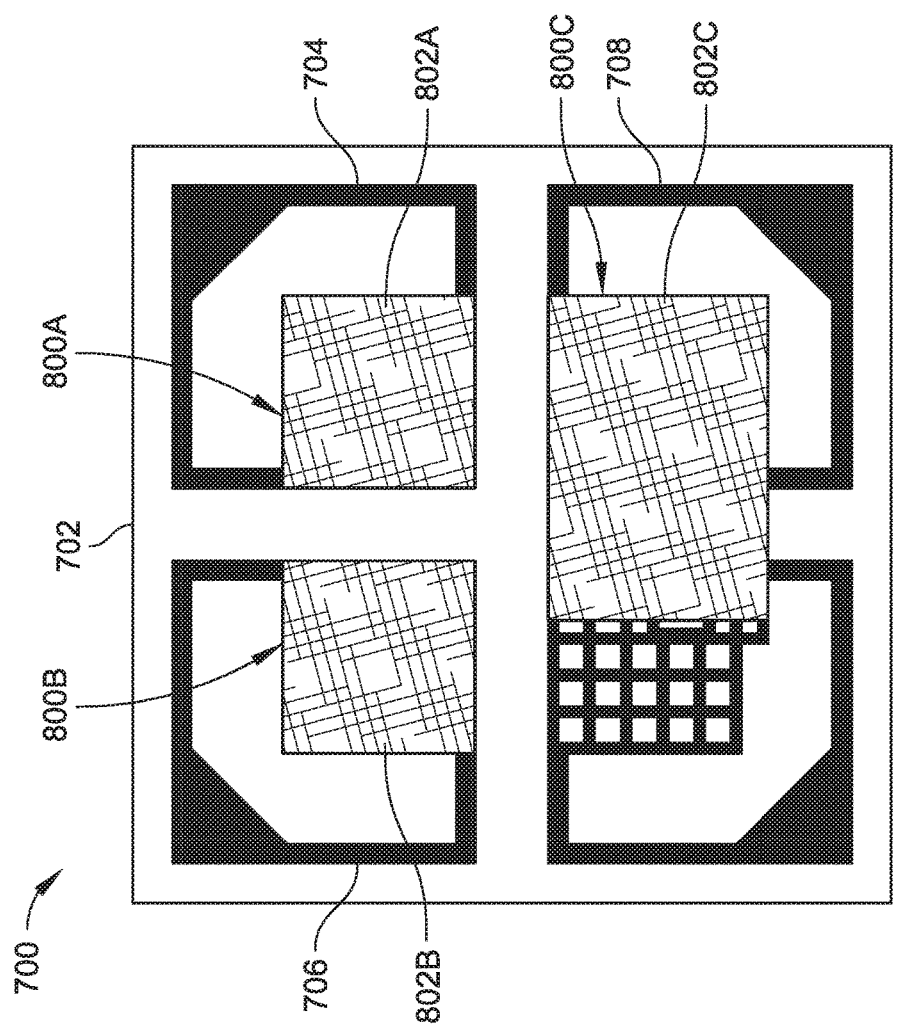

FIG. 9 is a bottom view of the lid assembly with Pt-Carbon paper adhered to reference, counter, and working electrodes, in accordance with an embodiment of this disclosure.

Figure 10:
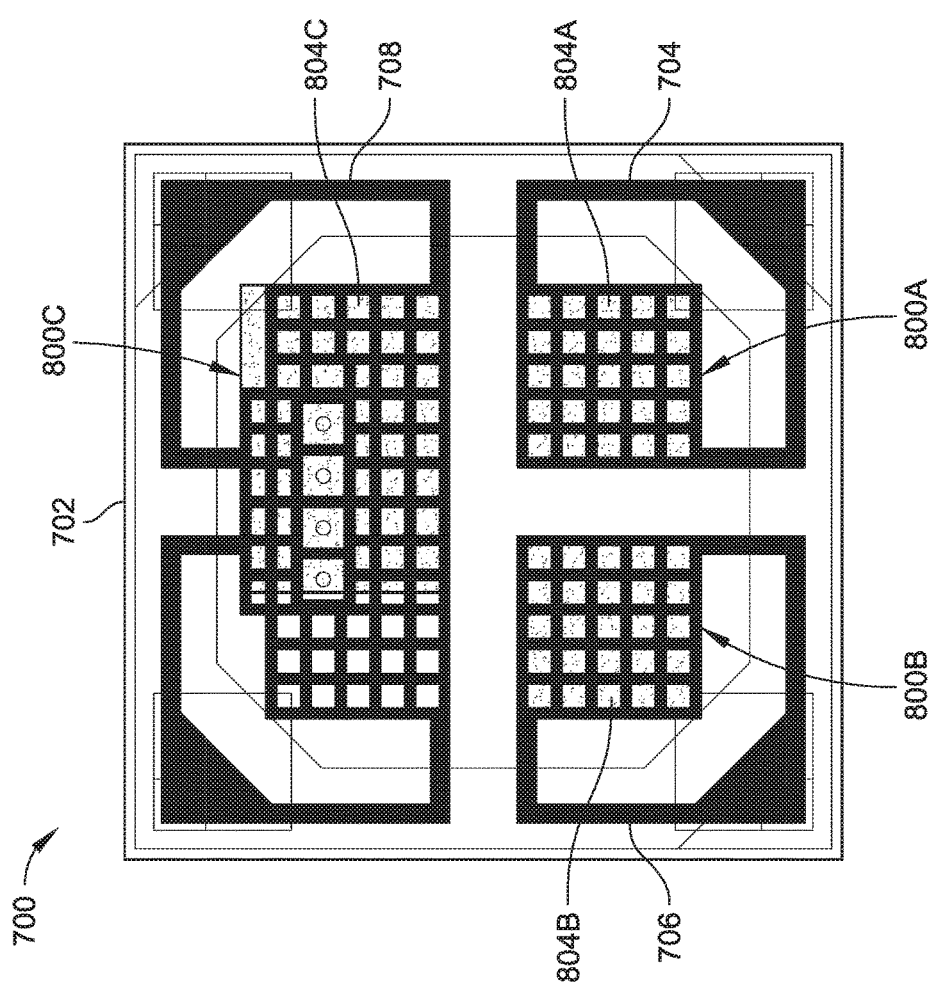

FIG. 10 is a top view of the lid assembly with Pt-Carbon paper adhered to reference, counter, and working electrodes, in accordance with an embodiment of this disclosure.

DETAILED DESCRIPTION

Overview

An electrochemical sensor/cell is a device capable of either deriving electrical energy from chemical reactions or facilitating chemical reactions through the introduction of electrical energy. Electrochemical sensors/cells are integral components of electrochemical sensors, which utilize electrodes to produce a current that is related to a detected amount of a molecular species, allowing for measurement of a relative amount or concentration the molecular species. Electrochemical sensors can be incorporated in devices that measure environmental pollutants such carbon monoxide detectors, and may also be used to measure breath alcohol. Because they require very little power to operate, electrochemical sensors have been widely used in personal safety devices that measure toxic gases.

Although electrochemical sensors meet the sensitivity, selectivity and power criteria for sensing gases, difficulty lies in producing sensors that are small enough to be suitable for mobile applications while still maintaining desired robustness, lifetime, and sensitivity needed. For example, care must be taken to avoid high temperature assembly steps that would evaporate the electrolyte. This can complicate assembly of micro-electrochemical cells, especially in arrays for air quality measurements, because of the need to seal the cell (except for the gas permeable membrane) and make electrical contacts, all at low temperature.

A mobile electrochemical air quality meter with one or more electrochemical sensors/cells for detecting one or more molecular species is described herein. In some implementations, an electrochemical sensor/cell includes a substrate with a cavity formed on a first side of the substrate, an ionic conductor (e.g., an electrolyte solution) is disposed within the cavity, and a lid assembly positioned over the cavity. The lid assembly may include a plurality of electrodes and a gas permeable or selectively permeable region positioned over the plurality of electrodes, where the plurality of electrodes include a working electrode configured to react a molecular species when the molecular species is received through the gas permeable region. The lid assembly may be sealed with the substrate with a bonding layer disposed between the lid assembly and the substrate. In some implementations, the bonding layer is curable with light or thermally curable at a suitably low temperature to avoid thermal damage to the ionic conductor or excessive evaporation of the electrolyte solution. Accordingly, right side-up (lid last) assembly is made possible. This can be an important feature where control circuitry (e.g., an ASIC) is coupled to a bottom side of the electrochemical sensor/cell. For example, the control circuitry may be connected to an underside of the substrate that is opposite the first side of the substrate. Where the control circuitry is coupled to an underside of a substrate (e.g., a glass/ceramic reservoir), a right-side up (lid last) assembly process may be required, where the ionic conductor is deposited prior to attachment of electrodes to electrical connections formed on the first side of the substrate, thereby connecting the electrodes to the control circuitry with vias going from the electrical connections through the substrate to respective electrical connections on the underside of the substrate.

In some embodiments, the electrochemical air quality meter includes a variety of cells with potentially different electrolytes, electrodes, and/or biases configured for detection of pollutants such as, but not limited to, $CO$, $NO_2$, $SO_2$, $O_3$, alcohols, formaldehyde, or a combination of gases. Multiple cells can be assembled onto a monolithic base into form factors like SIM-cards and micro-SD cards, with assembly processes occurring at low temperatures and protecting the electrolytes from interacting or reacting. For example, in some implementations which are described in greater detail below, the electrochemical air quality meter can include a plurality of electrochemical sensors/cells formed from a single (monolithic) substrate and a single (monolithic) panel, where the panel defines a plurality of lids disposed over respective cavities formed in the substrate. These cells can be separated or sealed from one another by the bonding layer. For example, the bonding layer may be an adhesive that defines a barrier between a first electrochemical sensor/cell and a second electrochemical sensor/cell, where each of the cells is defined by a cavity formed in the substrate and at least one lid defined by a portion of the panel that includes gas permeable region. To clarify, in this instance, the "lid" is the panel portion that covers the cavity of the electrochemical sensor/cell. Whether a separate structure or part of a monolithic panel, each lid can have a plurality of electrodes and a gas permeable region allowing at least one of the electrodes (e.g., a working electrode) to receive air flowing through the lid.

Example Implementations

FIGS. 1 through 6C illustrate an air quality meter 100 implemented in accordance with various embodiments of this disclosure. Those skilled in the art will appreciate that the embodiments illustrated in the drawings and/or described herein may be fully or partially combined to result in additional embodiments. Substitutions and other modifications can also be made without departing from the scope of this disclosure. Accordingly, the illustrated and described embodiments should be understood as explanatory and not as limitations of the present disclosure.

Figure 1:
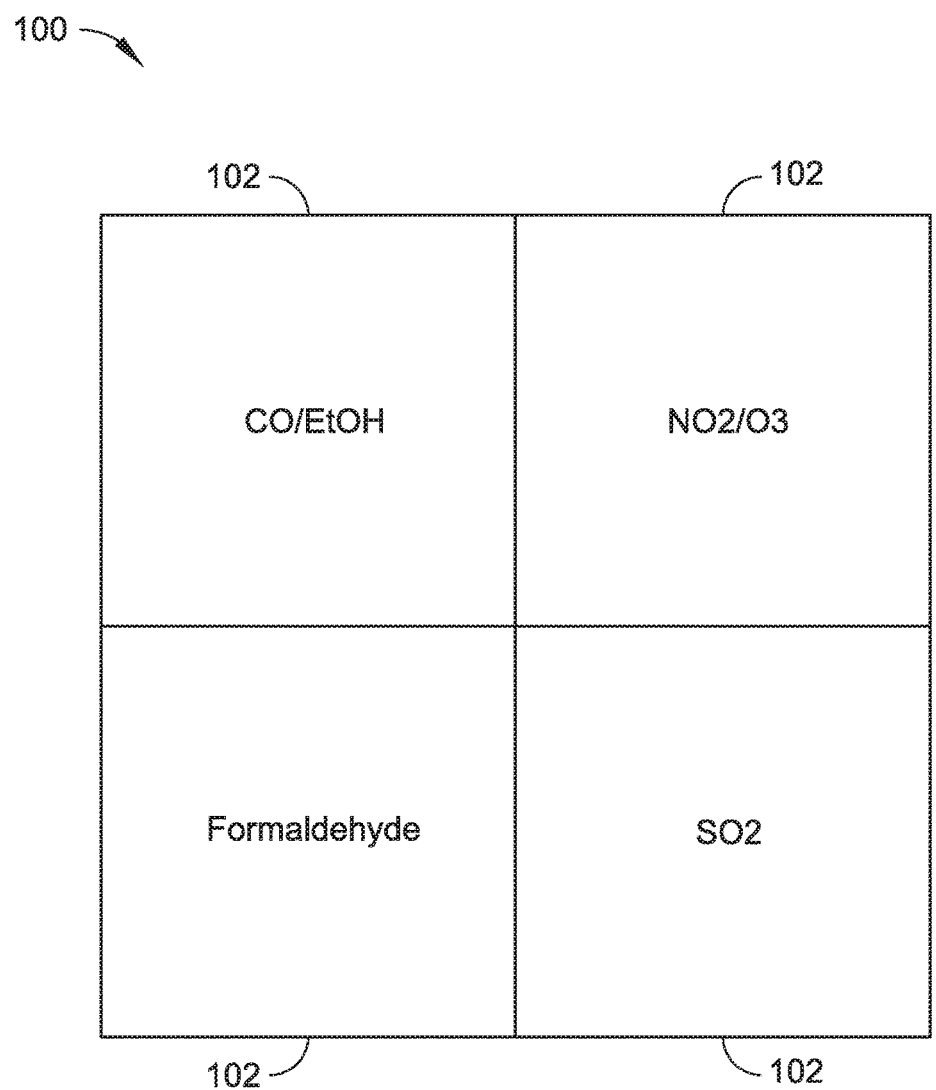
FIG. 1 is a schematic view of a multiple-sensor electrochemical air quality meter in accordance with an embodiment of this disclosure.

An embodiment of an air quality meter 100 is shown in FIG. 1, where the air quality meter 100 includes one or more electrochemical sensors/cells 102. The air quality meter 100 is shown to include a plurality of electrochemical sensors/cells 102 in FIG. 1. In some embodiments, the air quality meter 100 may include a single electrochemical sensor/cell 102. Each electrochemical sensor/cell 102 can be configured to detect one or more substances based on the electrolyte and/or electrodes associated with the gas sensor. For example, the electrochemical sensor/cell 102 can be configured to demonstrate sensitivity to one or more molecular species by filling a respective cavity of the gas sensor/cell 102 with an appropriate ionic conductor and sealing the cavity with an appropriate lid assembly. Examples of ionic conductors, without limitation, are polymer ionic conductors, acid and base electrolyte solutions and gels, and solid ionic conductors. In some embodiments, multiple electrochemical sensors/cells 102 are implemented by providing a plurality of cavities with respective electrolyte solutions and lids. Examples of molecular species detectable by an electrochemical sensor/cell 102 include, but are not limited to, CO, EtOH, $NO_2$, $O_3$, $SO_2$, Formaldehyde, a combination of the foregoing substances, or the like. The filling of the cavity can be done by placing an electrolyte gel on the lid and then assembling the lid to the substrate, or the electrolyte gel can be dispensed directly into the cavity. The gel does not need to fill the entire cavity. Air space or head room may be reserved to allow for long-term swelling and contraction of a hygroscopic electrolyte, such as sulfuric acid, in high or low humidity environments.

A lid assembly can include a plurality of electrodes (e.g., one or more working electrodes and one or more reference electrodes and/or counter electrodes). In the lid assembly, at least one working electrode is configured to react (e.g., oxidize or reduce) a molecular species coming into contact with the working electrode. This reaction generates or liberates ions which are mobile in the electrolyte solution and which diffuse or flow between the working electrode and at least one other electrode (e.g., reference electrode), where the resulting electrical diffusion current is indicative of a detected molecular species. For example, the resulting current can be used to determine a deposition or flow rate of the molecular species (e.g., gas species or aerosolized substance), a detected amount of the molecular species relative to a predetermined volume, or a detected amount of the molecular species relative to ambient air or other detected or predetermined levels of other molecular species (e.g., gases or aerosolized substances). As is well known in electrochemistry, at the other electrode (e.g., counter electrode), ions are neutralized with electrons, thus completing the circuit and completing the reaction. The ions may react at the counter electrode with a molecular species such as oxygen or hydrogen. To promote the reaction at the counter electrode, the ionic conductor may be prepared in a manner that facilitates both gas and liquid diffusion to the counter electrode. To promote electrical current flow and optionally select an appropriate reaction potential at the working electrode, a bias may be applied between the working and counter electrode, optionally relative to a reference electrode at the cell potential.

In some embodiments, a substrate (e.g., a glass, ceramic, or plastic substrate) is provided with multiple cavities and electrical connections. Lids are provided with one or more gas permeable regions positioned over the electrodes in a configuration that enables a molecular species to enter the lid through a gas permeable region and reach at least one working electrode. In some embodiments, separate lids or lid assemblies are provided for each electrochemical sensor/cell 102. In other embodiments, multiple lids are included in a common lid assembly or separate lid assemblies may share one or more components. For example, multiple lids can be implemented by a monolithic lid structure (e.g., a single panel), where the lids are separated by an adhesive or other barrier material between the cavities (e.g., between the cells 102) at junctions that seal the lid assembly to the substrate.

An ionic conductor may be provided for wicking of electrolyte to the electrodes. In some embodiments, the ionic conductor can comprise an ion conducting material such as a solid or polymer ionic liquid, such as Nafion or the like. In other embodiments, the ionic conductor can comprise a wick material and an electrolyte. The ionic conductor may provide both air and electrolyte transport between the electrodes. In some embodiments, a wick may have a surface area material (e.g., glass fiber) with suitably conductive liquid such as acid/base solution in water. The wick saturation level can be controlled by adding hydrophobic material (e.g., Teflon powder) to the wick to facilitate air communication and prevent saturation of the electrodes.

A low temperature thermal or light-cured adhesive can be provided to seal the lids to the substrate and isolate potentially different electrolytes. A low temperature thermal or light cured electrically conductive material can be used to connect the electrodes to the electrical connections on the substrate. In some embodiments, the seal and electrical conductive material can be the same, for example, a low temperature or UV-cured anisotropic conductive paste (ACP) or film (ACF). In some embodiments, the electrically conductive material can be carbon paste or carbon epoxy.

In some embodiments, the lid assembly can include holes through which electrical conductive material is dispensed after the lids are sealed. Lasers (e.g., optical lasers) can also be used to provide additional spot-curing of seal and/or electrically conductive material after dispense without heating the entire substrate or electrolyte disposed therein. In some embodiments, the electrically conductive material may be dispensed first to adhere to the electrodes via an aperture or gap in the lid assembly. Electrolyte gel and/or an ionic conductor (e.g., ion bridge/wick) may then be dispensed through the aperture or gap. A cover lid with gas permeable region may then be assembled over the top, followed by sealing with low temperature or UV-cure adhesive or photo-driven diffusion bonding.

In some embodiments, assembly can be performed at reduced temperature (e.g., via cryogenic assembly) and cure may occur when substrate and epoxy are brought to room temperature. This reduces miscibility of liquids (ice) prior to seal. The lid assembly can have laser or thermally activated adhesive which can be activated to seal by illuminating or heating to modest temperatures. Assembly may further include a filter placed over at least a portion of the cell cavity (e.g., over the entire cavity or over some regions and not others). Each cavity may include more than one gas permeable region and working electrode. For example, each cavity can have two or more working electrodes for increased sensitivity to a molecular species or for sensitivity to different gases or substances (e.g., a first working electrode sensitive to a first gas or aerosolized substance and a second working electrode sensitive to a second gas or aerosolized substance).

In some embodiments the bonding layer is a layer which forms a diffusion bond when activated. This bonding layer may include a dielectric, glass, metal, or other material which diffuses into the lid and substrate to form a bond. Diffusion may promoted by pressure, as well as heat or voltage. Fast laser pulses can deposit localized energy into a diffusion bond zone without thermally damaging the ionic conductor. Examples of diffusion bonding include plastic welding, Gold-Ge or Indium eutectic bonding and picosecond or femtosecond laser bonding. A transparent lid and/or substrate facilitates laser bonding. A patterned glass substrate and/or glass lid may be joined with a suitable diffusion bonding layer and laser illumination without damaging or evaporation the ionic conductor or electrolyte solution. In some embodiments, the substrate and lid comprise a fully liquid sealed ceramic package (e.g., in a similar fashion to a ceramic MOX sensor).

The foregoing assembly techniques are example processes that can be used to adhere the lid assembly and form connections between the electrodes and the electrical connections formed in the substrate. Importantly, assembly of some or all of the lid structures can be performed at reduced temperatures to avoid thermal damage of the ionic conductor and/or evaporation of the electrolyte solution. Suitable examples include, but are not limited to: low temperature or UV-cure ACP or ACF seal, low temperature or UV-cure seal ring with post-fill laser-cured vias, internal vias with post-fill epoxy, adhesive perimeter seal, or cryogenic assembly, or pico- or femtosecond laser diffusion bonding.

In embodiments, control circuitry (e.g., an ASIC or microcontroller) is connected to the electrical connections formed in the substrate to bias the one or more working electrodes and provide communications (e.g., detected current readings) to external circuitry (e.g., to a processor or controller/microcontroller of a mobile device). In some embodiments, the control circuitry is configured to independently bias each working electrode of a plurality of working electrodes associated with the one or more electrochemical sensors/cells 102 of the electrochemical air quality meter 100. In some embodiments, the substrate is connected with the control circuitry via a soldered plug assembly. In some embodiments, different electrodes and different electrolyte materials can be sealed into adjacent cavities on the same substrate with shared or separate respective electrical contacts, ASICs and connectors.

Figure 2:
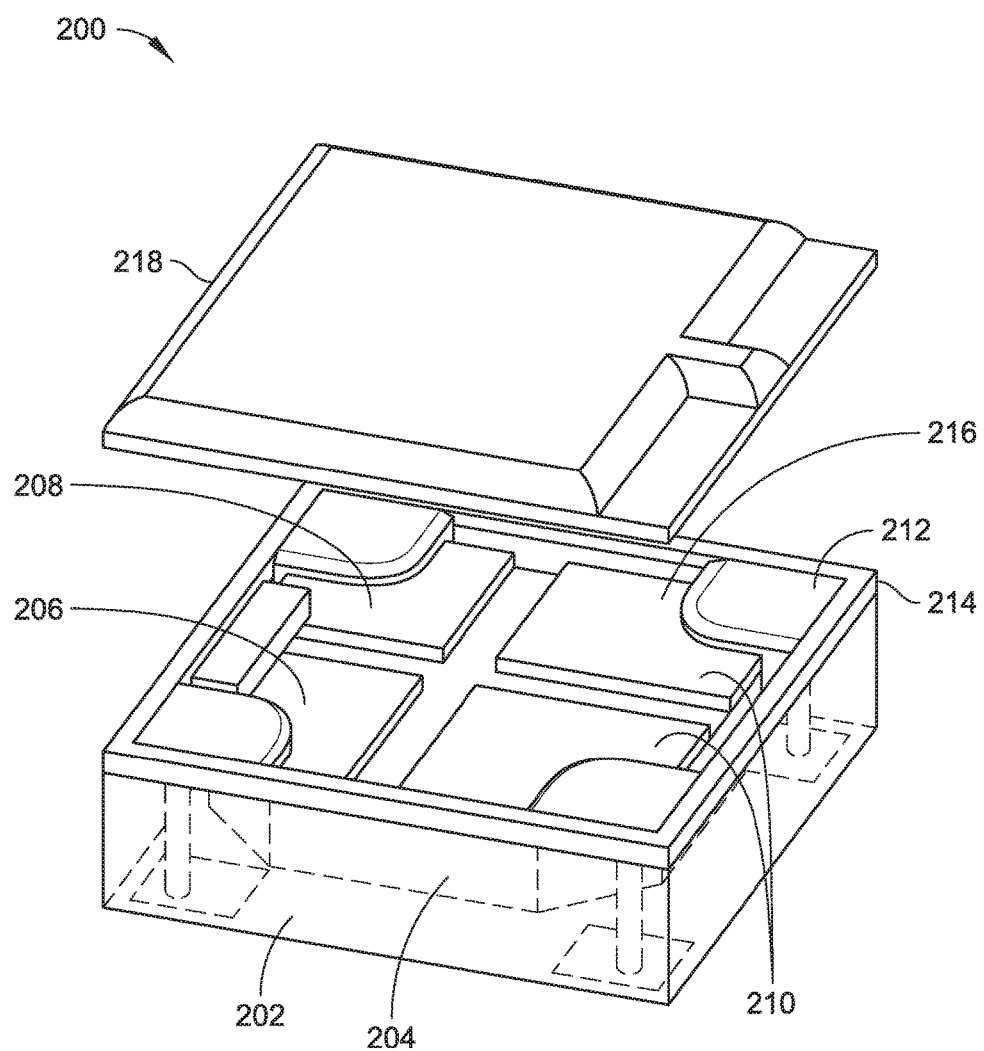
FIG. 2 is a partially exploded view of an electrochemical sensor/cell in accordance with an embodiment of this disclosure.

An electrochemical sensor/cell 200 is shown in FIG. 2 in accordance with an embodiment of this disclosure. The electrochemical sensor/cell 200 includes a printed circuit board (PCB) 202 configured to support electrical connections through a substrate 204 (e.g., glass, ceramic, or plastic substrate) to one or more electrodes (e.g., at least one working electrode 210, at least one reference electrode 208, and possibly a counter electrode 206). The electrodes may be formed in a lid assembly that is sealed to the substrate 204 with a light cured or low temperature thermally cured epoxy or adhesive paste 214. In some embodiments, the electrodes comprise platinum (Pt)-loaded carbon electrodes 216 coupled with a Nafion layer. Further, each electrode may have a carbon paste-based electrode 212 that partially or fully overlaps the electrode.

The lid assembly can include an epoxy-defined aperture 218 that enables molecular species and aerosolized substances to enter and flow towards the electrodes, wherein at least one working electrode 210 is enabled to react a molecular species, resulting in a current that travels through the electrical connections formed through the substrate 204 to respective electrical connections in the PCB 202.

Although a single sensor/cell 200 is shown in FIG. 2, in other embodiments, a plurality of sensor/cells 200 are formed by a substrate 204 having multiple cavities configured to contain electrolyte solution (e.g., all the same or possibly different electrolyte solutions). In some embodiments, the sensor/cells 200 have a common lid (e.g., a monolithic panel) sealed to the substrate 204 over multiple cavities formed therein. For example, each cavity can define a separate sensor/cell 200. The lid can have multiple apertures or gas permeable regions 218 allowing molecular species to travel through the lid and reach respective electrodes of each sensor/cell 200.

Control circuitry (e.g., an ASIC) may be coupled to the PCB 202 and configured to bias the one or more working electrodes and/or communicate signals or data indicative of the current resulting from the detected molecular species to an external controller (e.g., processor or microcontroller of a mobile device). In some embodiments, a common control circuitry (e.g., a common ASIC, microcontroller, microprocessor, or the like) is coupled to the electrodes (e.g., working electrodes 210, reference electrodes 208, and possibly counter electrodes 206) of respective ones of a plurality of sensors/cells 200 via electrical connections formed in the PCB 202, through the substrate 204, to the respective lid assembly of each sensor/cell 200.

Figure 3:
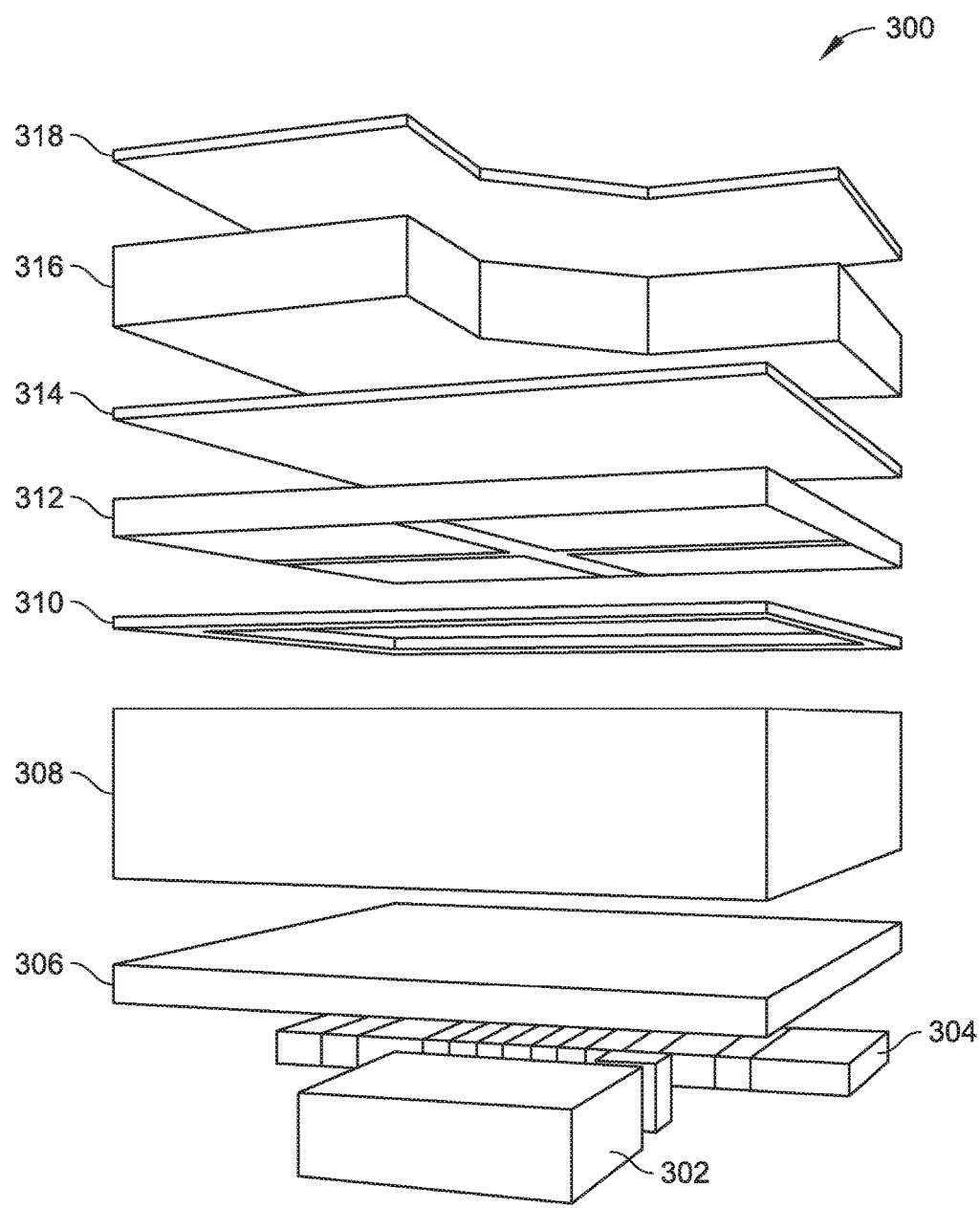
FIG. 3 is an exploded view of an electrochemical sensor/cell in accordance with an embodiment of this disclosure.

FIG. 3 shows another embodiment of an electrochemical sensor/cell 300. The electrochemical sensor/cell 300 may be manufactured according to a right-side-up assembly process, with control circuitry 302 (e.g., an ASIC, microcontroller, microprocessor, or the like) coupled to an underside of the electrochemical sensor/cell 300. For example, the control circuitry 302 can be coupled to electrical connections formed through a substrate 308. The control circuitry 302 can be coupled to the electrical connections via a connector 304. In some embodiments, the control circuitry 302 may be mounted to a PCB 306 that includes connections to the electrical connections (e.g., conductive vias) of the substrate 308.

In embodiments, the substrate 308 includes an electrolyte solution (e.g., electrolyte liquid/gel solution) or an ion conducting solid, liquid, or gel material. The substrate 308 may be coupled to the lid assembly with a light (e.g., UV light or laser) cured or low temperature thermally cured adhesive 310, such as ACP or ACF. An example of a suitably low curing temperature may include a temperature that does not induce or only includes minimal (e.g., less than about 25%) evaporation of the electrolyte solution contained in a cavity of the base 308. The amount of evaporation that is survivable depends on the type of electrolyte, for instance the molarity of an acid solution, which changes pH when water evaporates out of it.

The lid assembly may include a plurality of electrodes 312 (e.g., at least one working electrode, at least one reference electrode, and possibly a counter electrode). In some embodiments, the electrodes 312 are coated with or disposed adjacent to a layer of Nafion or any other ion-conducting material. The lid assembly may further include an aperture film 314, activated carbon paper/cloth 316, and/or a cover film 318 placed over the carbon cloth to define a lateral gas diffusion path from an input or edge of the activated carbon filter through the activated carbon volume to the input aperture. At least one gas permeable region may be defined through the lid assembly to enable at least one molecular species to permeate the lid assembly and reach the electrodes 312 (e.g., reaching at least one working electrode). At least one working electrode of the electrodes 312 will oxidize or reduce the molecular species, causing electrolytes to flow between the electrodes 312 and induce a current in the electrical connections running from the electrodes 312 to the control circuitry 302.

The control circuitry 302 can be configured to bias one or more of the electrodes 312 (e.g., biasing the working electrodes) and/or communicate signals or data indicative of the current resulting from the detected molecular species to an external controller (e.g., processor or microcontroller of a mobile device). In some embodiments, the control circuitry 302 is configured to determine a deposition or flow rate of the molecular species, a detected amount of the molecular species relative to a predetermined volume, or a detected amount of the molecular species relative to ambient air or other detected or predetermined levels of gases or aerosolized substances (e.g., gases/substances with known levels or detected by additional sensors/cells 300 making up an electrochemical sensor assembly).

As discussed above, in some embodiments, several electrochemical sensors/cells 300 are implemented in an electrochemical sensor assembly (e.g., air quality meter 100), were at least a portion of the lid assembly (e.g., a monolithic panel), the substrate 308 (e.g., multiple cavities), and/or the control circuitry 302 (e.g., a common ASIC, microcontroller, microprocessor, or the like) is shared among the sensors/cells 300 of a multiple-sensor electrochemical sensor assembly.

FIGS. 4A through 4H illustrate a process for assembling an electrochemical sensor/cell 400, such as electrochemical sensors/cells 200, 300, or 500 described herein. Thus, it is understood that the process may be modified to include assembly steps or operations required to form any electrochemical sensor/cell described herein, or required to carry out any of the assembly processes described herein. It is further noted that the embodiments of the air quality meter and/or electrochemical sensors/cells described herein are not intended as limitations of the present disclosure. The disclosure also contemplates any other electrochemical sensor/cell or assembly formed by the processes described herein.

Figure 4A:
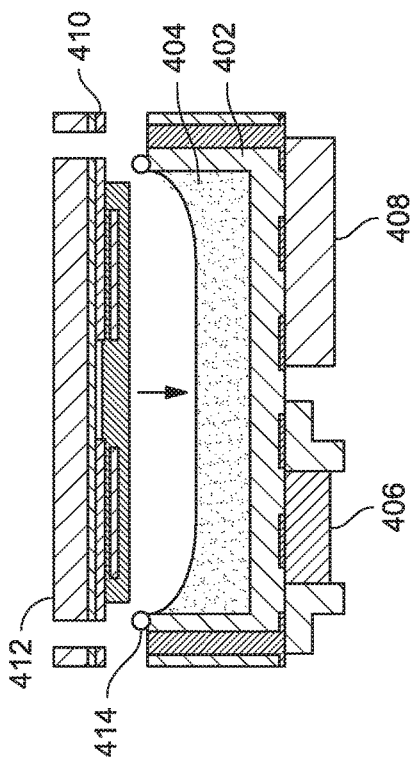
FIG. 4A illustrates a partially assembled electrochemical sensor/cell in accordance with an embodiment of this disclosure.

As shown in FIG. 4A, the process can include: reflowing electrical connections (e.g., from connector 408) and control circuitry connections (e.g., from ASIC 408 or a microcontroller, FPGA, or the like) to a substrate 402 (e.g., glass, ceramic, or plastic substrate); dispensing a thixotropic seal ring; and dispensing an electrolyte solution 404 (e.g., electrolyte gel or liquid) within a cavity of the substrate.

Figure 4B:
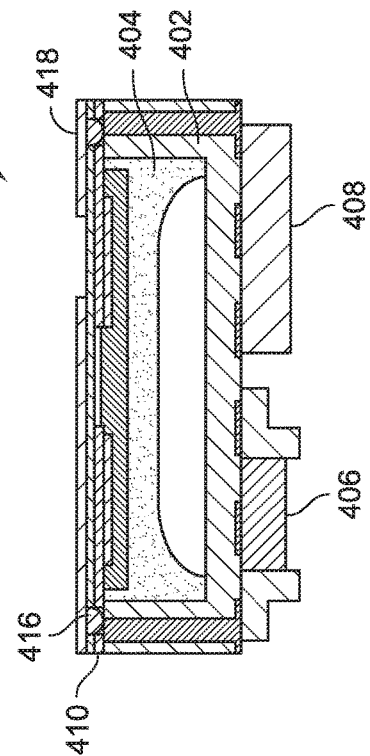
FIG. 4B illustrates a partially assembled electrochemical sensor/cell in accordance with an embodiment of this disclosure.

As shown in FIG. 4B, the process can further include: placing a lid 410 upon the substrate 402, the lid 410 including one or more holes; and curing with light (e.g., UV or laser curing) or thermally curing an epoxy 414, ACP/ACF, or other suitable adhesive at low temperature to adhere the lid 410 to the substrate 402. Afterwards, a support structure 412 used to handle and/or align the lid 410 can be removed.

Figure 4C:
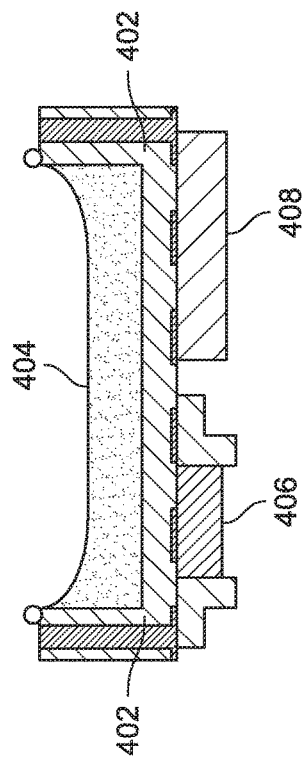
FIG. 4C illustrates a partially assembled electrochemical sensor/cell in accordance with an embodiment of this disclosure.

As shown in FIG. 4C, the process can further include: watering wicks to matrix on the lid 410; dispensing low viscosity conductive material 416 (e.g., conductive epoxy or ACP/ACF) into the holes in the lid 410 to connect electrodes in the lid 410 to electrical connections formed in the substrate 402; and laser curing the conductive material 416.

Figure 4D:
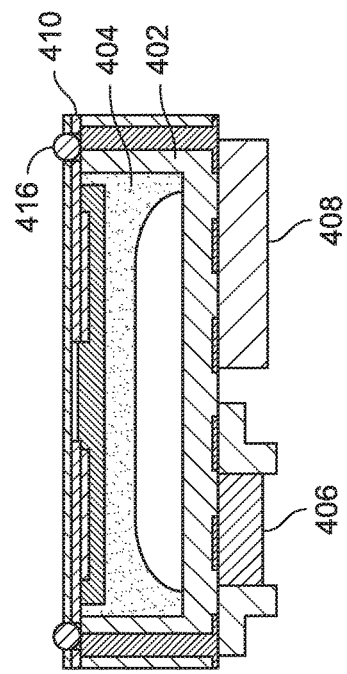
FIG. 4D illustrates a partially assembled electrochemical sensor/cell in accordance with an embodiment of this disclosure.

As shown in FIG. 4D, the process can further include laminating Kapton tape 418 to the lid 410 with an aperture formed over a permeable region to enable at least one molecular species to flow through the permeable region to one or more of the electrodes (e.g., to a working electrode). Another option is to assemble the lid 410, then fill the empty substrate vias with conductive material.

In some embodiments, a filter (e.g., activated carbon or charcoal filter) is placed over the electrochemical sensor/cell. FIGS. 4E through 4H illustrates optional process blocks for assembling a filter layer in the lid assembly of the electrochemical sensor/cell 400, where the process can further include process blocks for preparing "no-filter" regions in the resulting lid assembly.

Figure 4E:
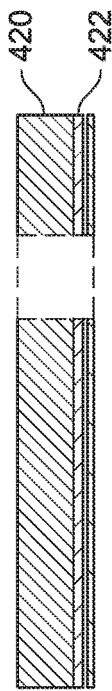
FIG. 4E illustrates a partially assembled electrochemical sensor/cell in accordance with an embodiment of this disclosure.

As shown in FIG. 4E, the process can include laminating a pressure-sensitive adhesive (PSA) 422 to carbon cloth/paper 420 that can then be placed over a gas permeable region of the lid. Optionally, the process can also include forming a no-filter region by removing a portion of the carbon cloth/paper 420 (e.g., as shown in FIG. 4F).

Figure 4F:
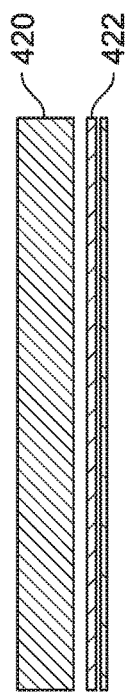
FIG. 4F illustrates a partially assembled electrochemical sensor/cell in accordance with an embodiment of this disclosure.
Figure 4G:
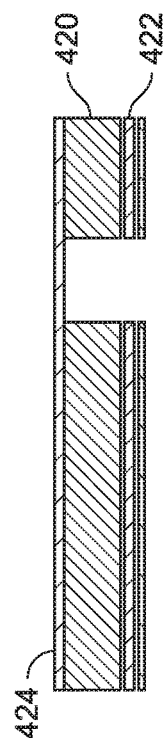
FIG. 4G illustrates a partially assembled electrochemical sensor/cell in accordance with an embodiment of this disclosure.
Figure 4H:
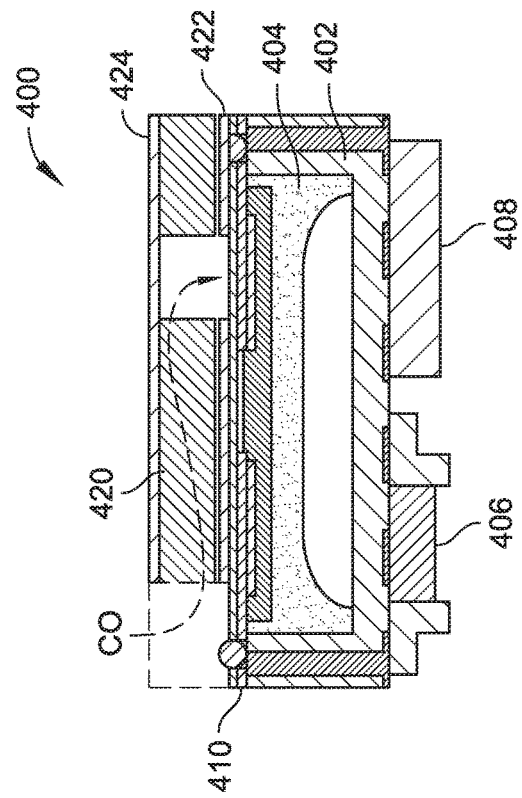
FIG. 4H illustrates an assembled electrochemical sensor/cell in accordance with an embodiment of this disclosure.

As shown in FIG. 4F, the process can include laminating the carbon cloth/paper 420 with Kapton tape 424 (e.g., instead of Kapton tape 418) placed on a side of the carbon cloth/paper 420 that is opposite the PSA 422. As shown in FIG. 4H, the PSA liner is removed and the PSA-coated side of the carbon cloth/paper 420 is laminated to the lid assembly by the PSA 422 (e.g., over the epoxy-defined aperture). In some implementations, the process further includes die cutting or laser cutting a corner of the carbon cloth/paper 420 to form an inlet for panel scale testing (e.g., as shown in FIG. 4H).

Figure 5:
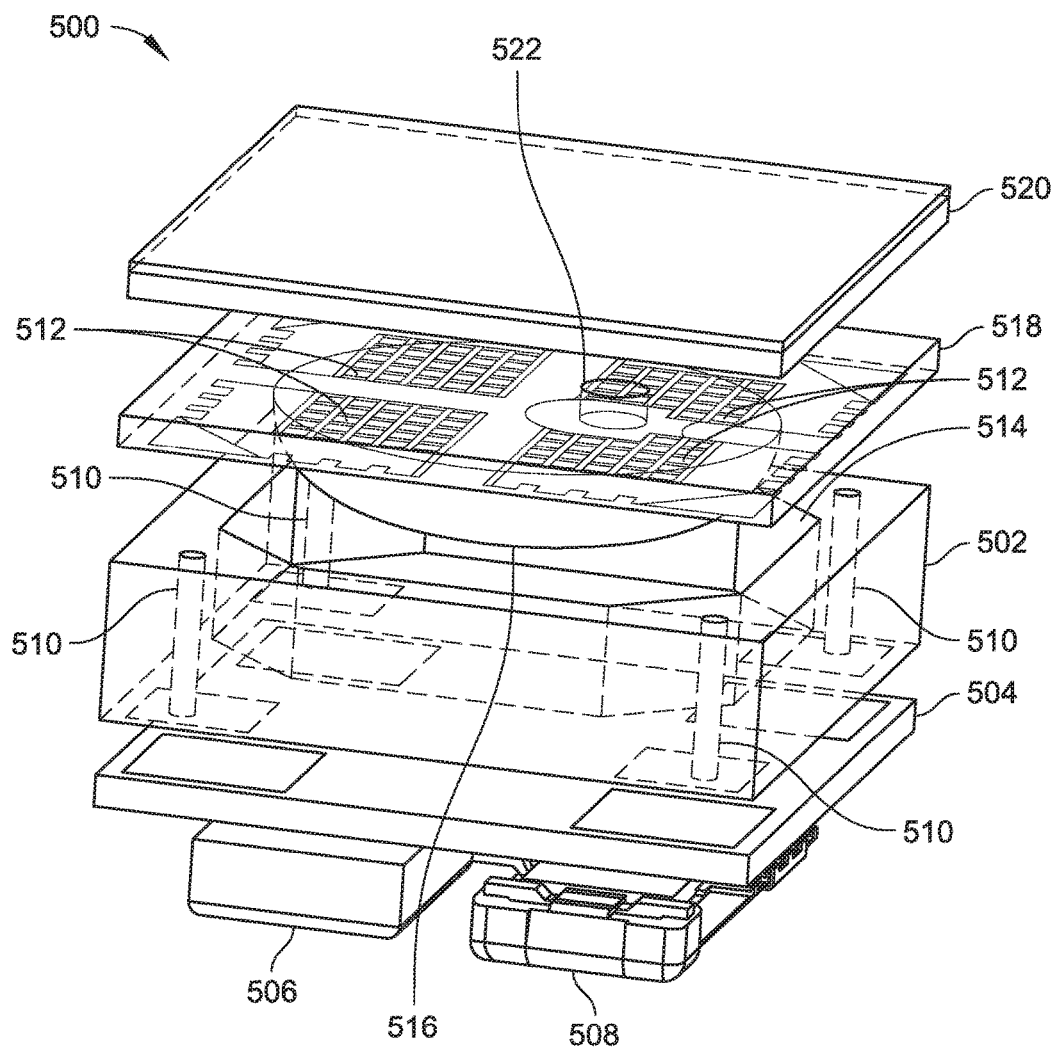
FIG. 5 is an exploded view of an electrochemical sensor/cell in accordance with an embodiment of this disclosure.

Looking now to FIG. 5, another embodiment of an electrochemical sensor/cell 500 is shown. The electrochemical sensor/cell 500 may be manufactured according to a right-side-up assembly process. For example, control circuitry 506 (e.g., an ASIC, microcontroller, microprocessor, or the like) and a connector 508 (for connecting to a mobile device main processor/microcontroller or the like) can be coupled to an underside of the electrochemical sensor/cell 500. The control circuitry 506 can be coupled to electrical connections (e.g., vias 510) formed through a substrate 502. In some embodiments, the control circuitry 506 and connector 508 may be mounted to a PCB 504 that includes connections to the electrical connections (e.g., conductive vias 510) of the substrate 502.

The substrate 502 includes a cavity configured to hold an ionic conductor 516, such as an electrolyte solution (e.g., electrolyte liquid/gel solution) or an ion conducting solid, liquid, or gel material. The substrate 502 may be coupled to a lid 518 with a light (e.g., UV light or laser) cured or low temperature thermally cured adhesive, such as ACP or ACF. An example of a suitably low curing temperature may include a temperature that does not induce or only includes minimal (e.g., less than about 25%) evaporation of an electrolyte solution contained in the cavity of substrate 502. The amount of evaporation that is survivable depends on the type of electrolyte, for instance the molarity of an acid solution, which changes pH when water evaporates out of it.

The lid 518 may include a plurality of electrodes 512 (e.g., at least one working electrode, at least one reference electrode, and possibly a counter electrode). In some embodiments, the electrodes 512 are coated with or disposed adjacent to a layer of Nafion or any other ion-conducting material. The lid 512 may further include an aperture 522 over a gas permeable region formed over the electrodes 512. The lid 512 can also be coupled to carbon paper/cloth 520, which may also be coupled to a cover film placed over the carbon cloth to define a lateral gas diffusion path from an input or edge of the activated carbon filter through the activated carbon volume to the input aperture 522. At least one gas permeable region may be defined through the lid assembly to enable at least one molecular species to permeate the lid assembly and reach the electrodes (e.g., reaching at least one working electrode). At least one working electrode of the electrodes 512 will oxidize or reduce the molecular species, causing electrolytes to flow between the electrodes 512 and induce a current in the electrical connections running from the electrodes 512 to the control circuitry 506.

The control circuitry 506 can be configured to bias one or more of the electrodes 512 (e.g., biasing the working electrodes) and/or communicate signals or data indicative of the current resulting from the detected molecular species to an external controller (e.g., processor or microcontroller of a mobile device). In some embodiments, the control circuitry 506 is configured to determine a deposition or flow rate of the molecular species, a detected amount of the molecular species relative to a predetermined volume, or a detected amount of the molecular species relative to ambient air or other detected or predetermined levels of gases or aerosolized substances (e.g., gases/substances with known levels or detected by additional sensors/cells 500 making up an electrochemical sensor assembly).

As discussed above, in some embodiments, several electrochemical sensors/cells 500 are implemented in an electrochemical sensor assembly (e.g., air quality meter 100), were at least a portion of the lid 518 (e.g., a monolithic panel), the substrate 502 (e.g., multiple cavities), and/or the control circuitry 506 (e.g., a common ASIC, microcontroller, microprocessor, or the like) is shared among the sensors/cells 500 of a multiple-sensor electrochemical sensor assembly.

FIGS. 6A through 6C illustrate a process for assembling an electrochemical sensor/cell 600, such as electrochemical sensors/cells 200, 300, or 500 described herein. Thus, it is understood that the process may be modified to include assembly steps or operations required to form any electrochemical sensor/cell described herein, or required to carry out any of the assembly processes described herein. It is further noted that the embodiments of the air quality meter and/or electrochemical sensors/cells described herein are not intended as limitations of the present disclosure. The disclosure also contemplates any other electrochemical sensor/cell or assembly formed by the processes described herein.

As shown in FIGS. 6A through 6C, a conductive adhesive 606 (e.g., ACP, ACF, or the like) can be used to bond a lid 602, such as the lids or lid assemblies described above, to a substrate 610 having at least one cavity for receiving an ionic conductor 608 (e.g., electrolyte solution). The conductive adhesive 606 seals the lid 602 and the substrate 610 together, and in addition, the conductive adhesive 606 electrically couples electrodes 604 in the lid 602 to electrical connections (e.g., conductive vias 612) going through the substrate 610. In some implementations, the vias 612 enable connection from the electrodes 604 to a PCB disposed beneath substrate 610. Control circuitry (e.g., an ASIC, microcontroller, or the like) and/or one or more connectors (e.g., 10-pin connectors, etc.) may be mounted to the PCB.

FIG. 6B shows how conductive particles in the conductive adhesive 606 are pressed together to create conductive paths in the direction of applied pressure when the conductive adhesive 606 is compressed (e.g., when the lid 602 is sealed with the substrate 610). The conductive adhesive 606 can be cured at low temperature, for example, utilizing a Femtosecond laser 614 (e.g., as shown in FIG. 6C), or utilizing any other low temperature or light activated curing technique.

FIG. 7 shows a lid assembly 700 in accordance with another embodiment of this disclosure. The lid assembly 700 includes a glass or ceramic panel 702 with a counter electrode 704, a reference electrode 706, and a working electrode 708 disposed upon the panel 702. In some embodiments, the electrodes 704, 706, and 708 can be printed on the panel 702 or otherwise adhered to the panel 702. The panel 702 can also include one or more apertures 710 (e.g., four apertures in the illustrated embodiment) for gas flow through the lid assembly 710.

To enable detection of gases in a form factor compatible with mobile requires not just making the overall sensor package smaller, but also changing sensor geometries, design and assembly. Core to operation of electrochemical gas sensors is an implemented three-phase interface. A paste that creates a three-phase interface can be used. For example, the paste can be formulated from platinum, hydrophobic materials such as Teflon, and a scaffold such as glass fiber.

In some embodiments, Pt-Carbon membranes (such as those used for fuel cells) can be used to implement a three-phase interface in the lid assembly 700. The three-phase interface (e.g., portions 800A, 800B, and 800C in FIGS. 9 and 10) is a multi-layer structure comprising a hydrophobic layer (e.g., carbon paper or cloth) and a catalyst layer (e.g., platinum). For example, FIG. 8A shows a platinum (Pt) loaded side 802 of a Pt-Carbon paper 800, and FIG. 8B shows a non-Pt loaded side 804 of the Pt-Carbon paper 800. These membranes can be singulated and attached to the electrode interconnects the sensor package. As discussed herein, the package itself can be fabricated from photostructural glass or any other chemically resistant materials such as regular fused silica and fused ceramic materials like alumina. These membranes can be mounted with standard assembly pick and place techniques. The membranes are attached in a way to ensure the side of the electrodes that face the incoming gas remains dry. This can be done by sealing these electrodes against the lid, package sidewalls and base well through various methods including epoxies, and sputtered metals.

FIG. 9 is a bottom view of the lid assembly 700 with Pt-Carbon paper 800 (e.g., paper cutouts 800A, 800B, 800C) adhered to exposed surfaces of the counter electrode 704, reference electrode 706, and working electrode 708 with the Pt-loaded side (e.g., surfaces 802A, 802B, and 802C) facing away from the electrodes. In some embodiments, the Pt-Carbon paper covers only a portion of each electrode. In other embodiments, substantially all of the electrode grid is covered by the Pt-Carbon paper 800 (e.g., as shown for the counter electrode 704 and the reference electrode 706 in FIG. 9). The three-phase interface (e.g., the Pt-Carbon paper 800 or the like) can also be mounted over/under the one or more apertures 710 of the lid assembly 700. FIG. 10 is a top view of the lid assembly 700 with Pt-Carbon paper 800 adhered to the electrodes. In FIG. 10 it is shown that from a top view, the non-Pt loaded side (e.g., surfaces 804A, 804B, and 804C of cutouts 800A, 800B, and 800C) are facing the electrodes, effectively placing the electrodes between the Pt-Carbon paper 800 and the panel 702 of the lid assembly 700.

Those skilled in the art will appreciate that any embodiment of the disclosure manifested above as a system or method may include at least a portion of any other embodiment described herein. Those having skill in the art will also appreciate that there are various embodiments by which systems and methods described herein can be implemented, and that the implementation will vary with the context in which an embodiment of the disclosure is deployed. Furthermore, it is to be understood that the invention is defined by the appended claims. Although embodiments of this invention have been illustrated, it is apparent that various modifications may be made by those skilled in the art without departing from the scope and spirit of the disclosure.

What is claimed is:

1. An electrochemical cell, comprising:
a substrate with a cavity formed on a first side of the substrate, the substrate including vias extending through outer edges of the substrate, from a top to a bottom of the substrate;
an ionic conductor disposed within the cavity; and
a lid assembly positioned over the cavity, the lid assembly including a plurality of electrodes attached to a glass or ceramic panel, the glass or ceramic panel having one or more apertures, the plurality of electrodes including a working electrode configured to react with a molecular species that diffuses through the one or more apertures, wherein said reaction produces ions mobile in the ionic conductor between two or more of the plurality of electrodes, the lid assembly further including a three-phase interface positioned over at least a portion of the plurality of electrodes, wherein the plurality of electrodes are at least partially positioned in between the three-phase interface and the glass or ceramic panel of the lid assembly.

2. The electrochemical cell of claim 1, wherein the three-phase interface is also positioned over at least a portion of the one or more apertures.

3. The electrochemical cell of claim 1, wherein the three-phase interface comprises a multi-layer interface including at least a hydrophobic layer and a catalyst layer.

4. The electrochemical cell of claim 1, wherein the three-phase interface comprises Pt-Carbon paper.

5. The electrochemical cell of claim 4, wherein a Pt-loaded side of the Pt-Carbon paper faces away from the plurality of electrodes.

6. The electrochemical cell of claim 4, wherein a non-Pt-loaded side of the Pt-Carbon paper faces the plurality of electrodes.

7. The electrochemical cell of claim 1, further comprising control circuitry coupled to an underside of the substrate, where the underside of the substrate is opposite an upper side of the substrate that is coupled to the lid assembly, the control circuitry being electrically connected to the one or more of the electrodes by the vias extending through the outer edges of the substrate.

8. The electrochemical cell of claim 7, further comprising an electrical connector coupled to the underside of the substrate, the electrical connector being configured to connect the control circuitry to a controller or processor.

9. The electrochemical cell of claim 1, wherein the substrate comprises a ceramic or glass substrate.

10. An electrochemical sensor assembly, comprising:
a substrate with a plurality of cavities and electrical connections formed on a first side of the substrate;
one or more electrolyte solutions disposed within the plurality of cavities;
a lid assembly positioned over the plurality of cavities, the lid assembly including a plurality of electrodes attached to a glass or ceramic panel, the glass or ceramic panel having one or more apertures, the plurality of electrodes including a plurality of working electrodes configured to react respective molecular species when a molecular species is received by a respective one of the plurality of working electrodes through the one or more apertures, wherein said reaction produces ions mobile in the ionic conductor between two or more of the plurality of electrodes, the lid assembly further including a three-phase interface positioned over at least a portion of the plurality of electrodes; and
control circuitry connected to one or more of the plurality of electrodes via the electrical connections going through the substrate.

11. The electrochemical sensor assembly of claim 10, wherein the plurality of working electrodes include a first working electrode configured to react with a first molecular species and a second working electrode configured to react with a second molecular species different from the first molecular species, the first working electrode is associated with a first cavity of the plurality of cavities and the second working electrode is associated with a second cavity of the plurality of cavities.

12. The electrochemical sensor assembly of claim 11, wherein the first cavity is filled with a first electrolyte solution and the second cavity is filled with a second electrolyte solution different from the first electrolyte solution.

13. The electrochemical sensor assembly of claim 10, wherein the three-phase interface is also positioned over at least a portion of the one or more apertures.

14. The electrochemical sensor assembly of claim 10, wherein the plurality of electrodes are at least partially positioned in between the three-phase interface and the glass or ceramic panel of the lid assembly.

15. The electrochemical sensor assembly of claim 10, wherein the three-phase interface comprises a multi-layer interface including at least a hydrophobic layer and a catalyst layer.

16. The electrochemical sensor assembly of claim 10, wherein the three-phase interface comprises Pt-Carbon paper.

17. The electrochemical sensor assembly of claim 16, wherein a Pt-loaded side of the Pt-Carbon paper faces away from the plurality of electrodes.

18. The electrochemical sensor assembly of claim 16, wherein a non-Pt-loaded side of the Pt-Carbon paper faces the plurality of electrodes.

19. A lid assembly, comprising:
a glass or ceramic panel, the glass or ceramic panel having one or more apertures;
a plurality of electrodes attached to the glass or ceramic panel, the plurality of electrodes including a working electrode configured to react with a molecular species that diffuses through the one or more apertures; and
a multi-layer three-phase interface positioned over at least a portion of the plurality of electrodes, the multi-layer three-phase interface including at least a hydrophobic layer and a catalyst layer.

* * * * *